United States Patent [19]
Rowe-Lanzisera et al.

[11] Patent Number: 5,405,357
[45] Date of Patent: Apr. 11, 1995

[54] ACUPRESSURE GLOVE DEVICE

[76] Inventors: Lisa Rowe-Lanzisera; Frank Lanzisera, both of 8008 18th Ave. W., Bradenton, Fla. 34209

[21] Appl. No.: 124,791

[22] Filed: Sep. 22, 1993

[51] Int. Cl.⁶ .............................................. A61B 17/00
[52] U.S. Cl. ........................................ 606/204; 2/160
[58] Field of Search ................... 606/201, 204; 128/26, 128/24 R; 2/158-169

[56] References Cited

U.S. PATENT DOCUMENTS 4,233,966 11/1980 Takahashi .
4,520,798 6/1985 Lewis .
5,067,478 11/1991 Berlant .
5,199,876 4/1993 Waldman .

FOREIGN PATENT DOCUMENTS 3819859 12/1989 Germany .......................... 606/204

Primary Examiner—Stephen C. Pellegrino
Assistant Examiner—William W. Lewis

[57] ABSTRACT

An acupressure glove enabling safe, accurate and cost-effective application of self-stimulation of acupressure points on the hand and wrist. By producing direct pressure onto an acupressure point via a specifically positioned nodule on the glove's interior surface and guided by the corresponding color-coded locator on the glove's exterior surface an individual can utilize acupressure therapy for a variety of physical complaints. The physical complaints can be comprised of carpal tunnel syndrome, golfer's and tennis elbow, general pain, acute and chronic neck pain, headache, and stress and anxiety.

6 Claims, 17 Drawing Sheets

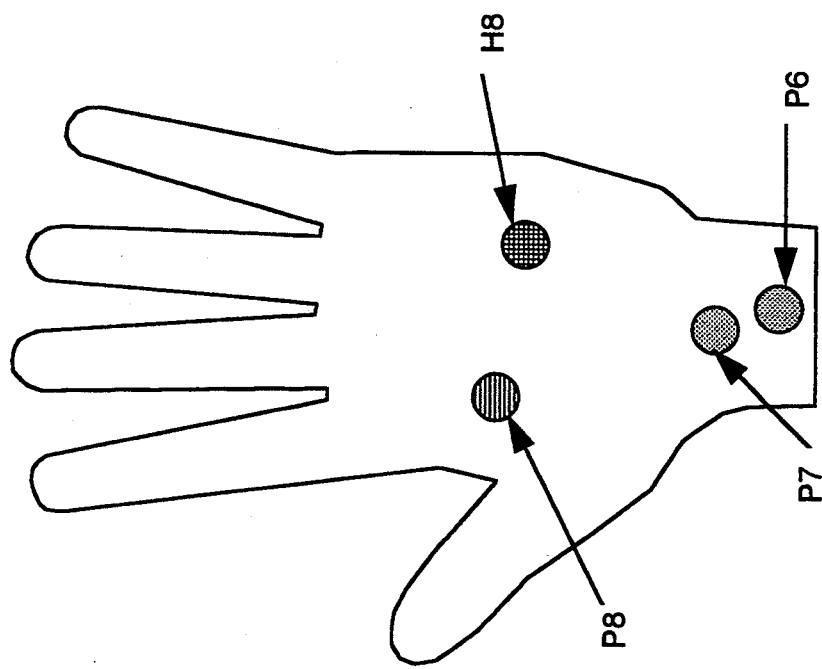

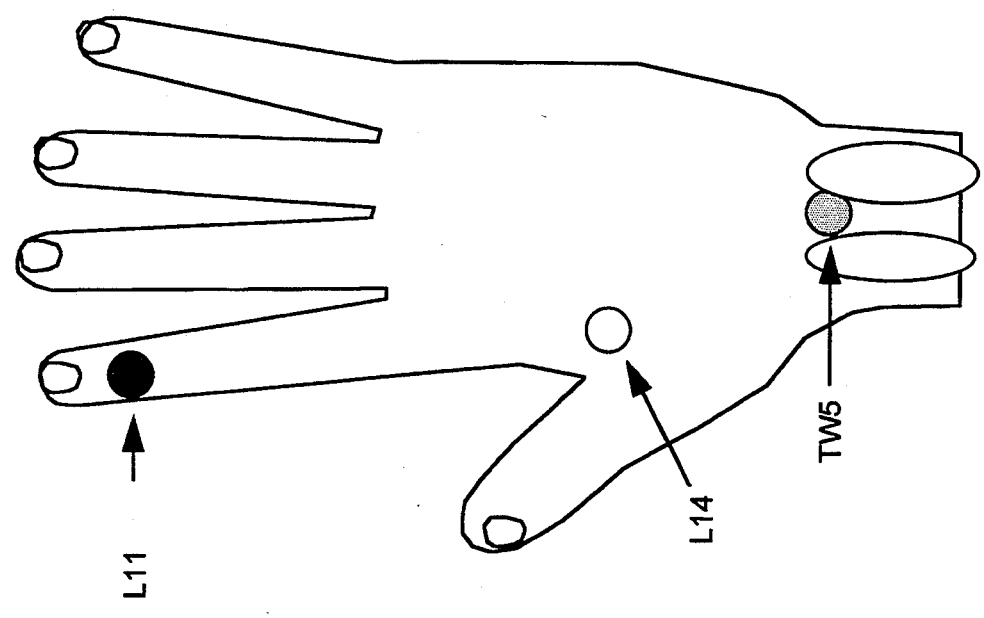
Figure 10-B

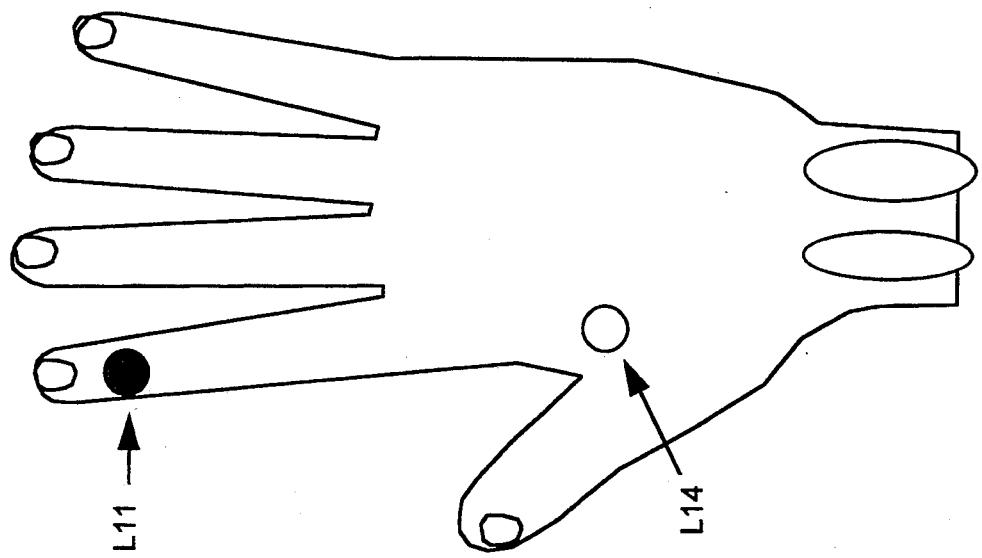
Figure 10-C

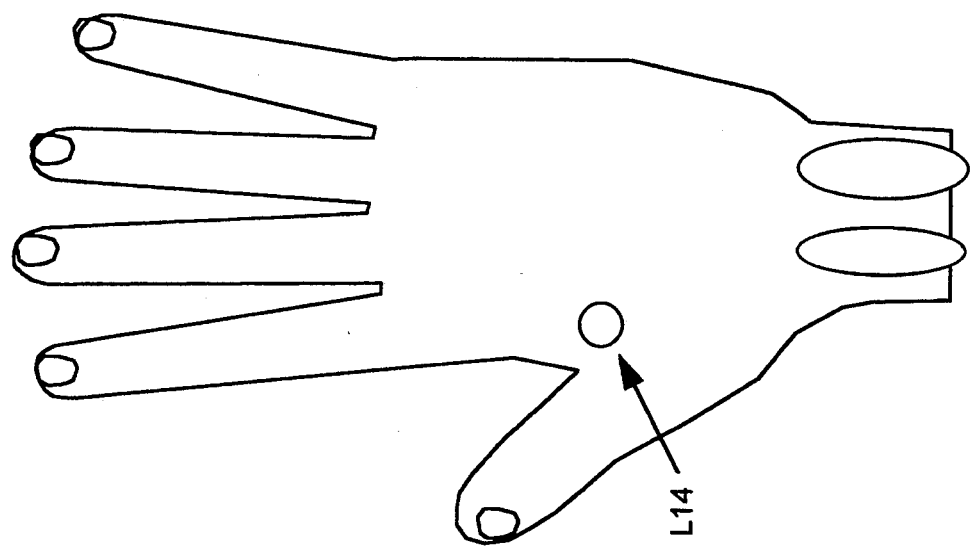
Figure 10-D

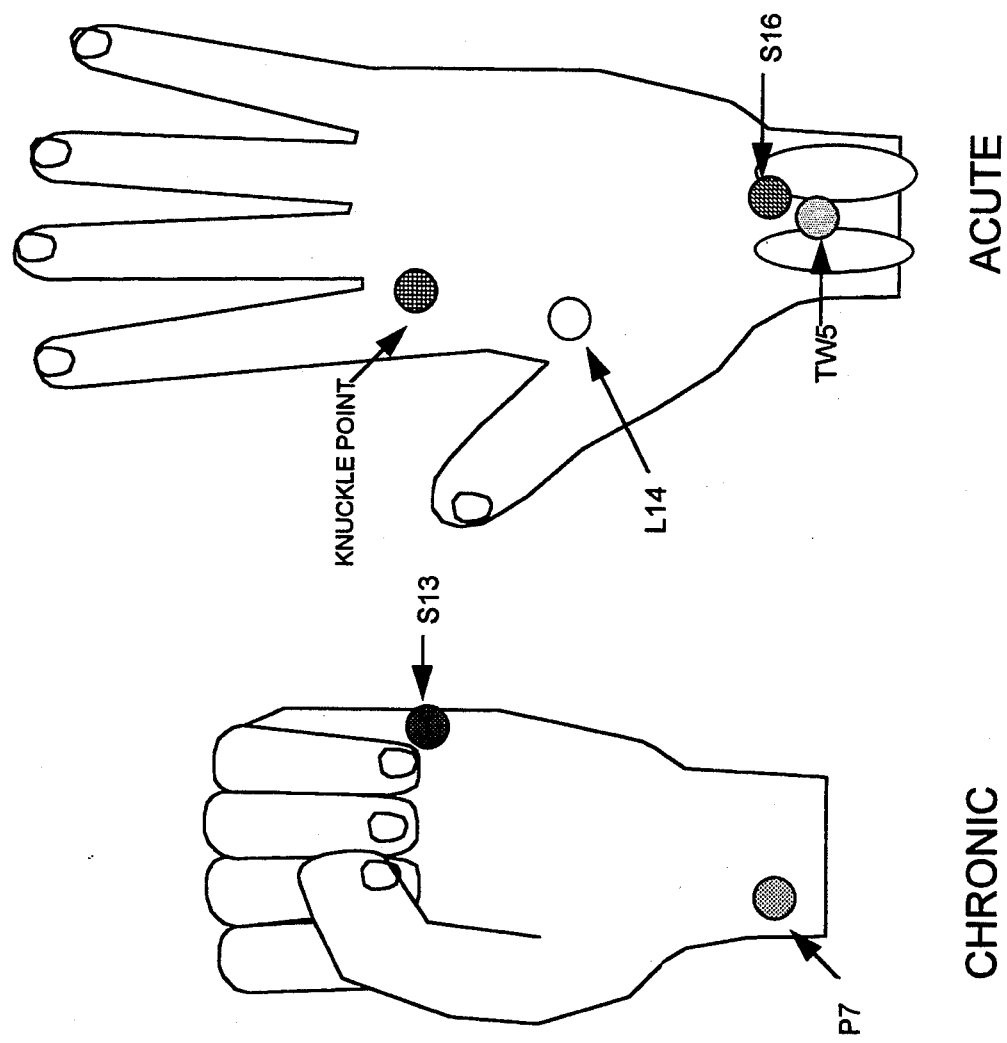
Figure 10-E

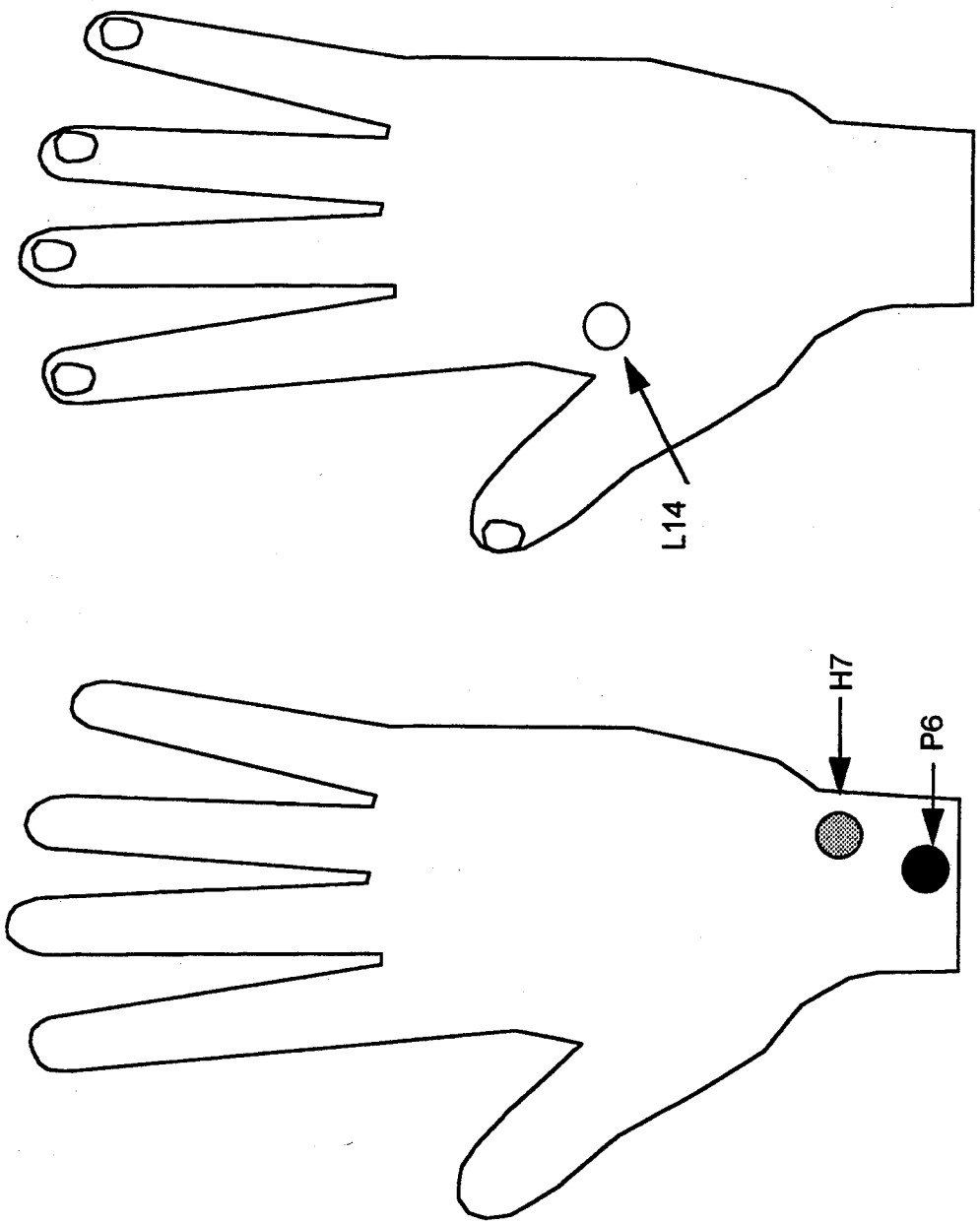
Figure 10-F

ACUPRESSURE GLOVE DEVICE

BACKGROUND OF THE INVENTION

1. Field of the Invention

This invention is a device for non-invasive auto-stimulation of acupressure points on the dorsal and palmar surfaces of the hands and fingers. More specifically, a glove, conforming to anatomical contours, is fitted on its interior surface area with nodules that, when worn by an individual, are positioned over acupressure points of the hand, wrist, and fingers. Gloves are to be worn on both the right and left. The individual, after pulling the gloves on snugly, applies direct pressure to locators on the exterior surface area of the glove which are attached through the glove to the underlying nodules. Stimulation of acupressure points via direct pressure produces a positive reaction by the body for a plurality of physical complaints.

2. Prior Art

Acupressure, a non-invasive form of acupuncture is accepted by the medical community and the general public, as a valid form of treatment. Individuals seeking a non-drug approach for a plurality of physical complaints find acupressure therapy a safe and cost-effective alternative.

This invention relates to a glove for auto-stimulation of acupressure points on the hands, fingers and wrists using direct pressure on nodules located on the glove's interior surface area. Automatic correct placement of these nodules over the acupressure points is accomplished by a flexible, elastic glove that conforms to a typical hand's bony and soft-tissue contours. These nodules are identified on the glove's exterior surface by locators. The individual then only has to refer to the enclosed chart for their physical complaint and corresponding acupressure point(s) to safely and accurately apply acupressure therapy via direct pressure. This invention allows an individual to accurately apply acupressure therapy without having to rely on other guides or having specific anatomical knowledge of the hand, wrist, and fingers.

In order to provide background information so that the invention may be completely understood and appreciated in its proper context, reference is made to a number of prior art patents as follows:

U.S. Pat. No. 4,233,966 is an "Appliance for Use in Acupressure Therapy" and is used for applying finger pressure therapy to one's self. It consists of a holder with variable protuberances. The individual then lays atop the holder producing pressure on "particularized areas established in accordance with knowledge of finger pressure therapy." The user of this invention must be knowledgeable in the correct configuration of the protuberance as well as anatomical landmarks to accurately position the holder. The shortcomings of this invention rests in the average person's general lack of knowledge of anatomy and acupressure therapy. Also, the holder is an obvious departure from the present invention's mode of application which is a glove.

U.S. Pat. No. 4,520,798 is an apparatus for self-administration of acupressure points. It is wall mounted with adjustable arms which end with a knob member that the user presses against with his body. The drawback of this device is that it is not portable and requires knowledge of anatomy and acupressure point locations that the average individual lacks. It also does not refer to acupressure points of the hand, wrist, and fingers.

U.S. Pat. No. 5,067,478 is an electrode glove used for applying TENS and massage or acupressure to a second individual. It is designed to be used by a clinician, the glove is attached to a transcutaneous electrical nerve stimulation unit (TENS) producing an "electro-touch". The inherent disadvantage of this form lies in its need to be administered by a second skilled person. Also, specific acupressure points are not affected. Rather, the whole hand receives an electrical current. In addition, introducing a focalised electrical charge onto the skin can produce a superficial burn.

U.S. Pat. No. 5,199,876 is a hand reflexology glove imprinted with a reflexology zone map. The glove overlays organ and bodily function reflex receptor zone points. There is no mention of acupressure or acupuncture in this patent. Rather, this invention deals entirely with reflexology which departs from the science of acupressure.

Whatever the precise merits, features, and advantages of the above cited reference none achieves or fulfills the purpose of the acupressure glove, the present invention.

SUMMARY OF THE INVENTION

This invention is a specially-designed glove for self-applying acupressure therapy to the hands, wrists, and fingers via direct pressure.

Accordingly, it is the principal object of the present invention to provide a safe, accurate, and cost-effective means of self-applying acupressure therapy. Specifically, acupressure points on the hands, wrists, and fingers can be located and direct pressure easily applied to these points by proper use of these specially-designed gloves. The interior of the glove is fitted with nodules positioned over acupressure points when worn. The user can apply direct pressure to these points using corresponding locators on the exterior of the glove as guides.

Another object of this invention is to stimulate the acupressure points by the safest method known, i.e., self-application of mild, direct pressure. By not using more hazardous means of stimulation, such as electricity, the user can safely apply acupressure therapy to one's self. Another advantage of using non-electrical stimulation is the portability of this invention. The individual can wear the glove while continuing to work and move about without restricting wires.

A further object is to provide an individual with the means of accurately applying acupressure therapy without needing to refer to a separate guide. The present invention eliminates the need to refer to an anatomical chart or acupressure point guide each time acupressure therapy is performed. The individual identifies the acupressure points for his particular physical complaint by using an enclosed guide and either removes or ignores the locators and nodules that do not pertain. Locators and nodules can be replaced in their proper site by guide holes in the glove. Each locator is color-coded with reference by location on an enclosed guide so that the individual can be assured that he is stimulating the correct acupressure point.

The above objects are realized in a snug-fitting glove having individual fingers with the nodules positioned inside the glove corresponding to acupressure points on the hand, wrist and finger. Color coded locators on the outside of the glove identify the underlying acupressure points. By applying a mild direct pressure over the locator, an individual stimulates the underlying acupressure point via the nodule.

DESCRIPTION OF DRAWING FIGURES

All drawings illustrating this invention in its preferred and alternate embodiments portray the glove as being constructed of a flexible, elastic material such as a combination of nylon and spandex with the locators and nodules being made of a durable plastic material.

FIG. 10 is a perspective view illustrating particular acupressure points and their associated physical complaints.

DETAILED DESCRIPTION OF THE INVENTION

Figure 1:
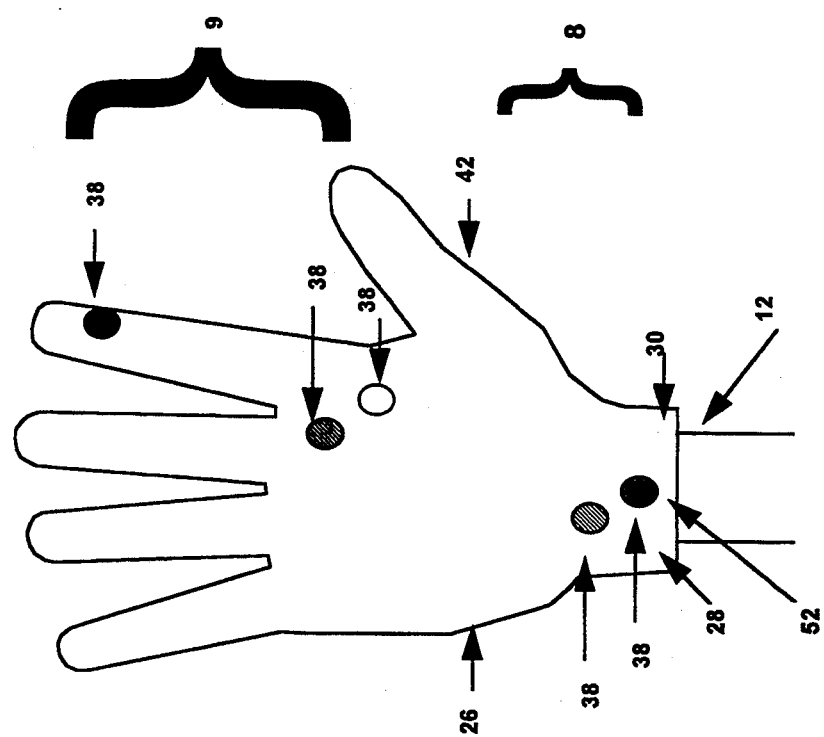
FIG. 1 is a perspective dorsal view of the preferred embodiment covering the left hand, wrist, and fingers illustrating the distribution of the acupressure point locators.

The acupressure treatment device, in the form of an acupressure glove 42, is comprised of an elastic, flexible form capable of conforming to a human hand 12,7 and wrist 8, and nodules 39 which are removably embedded on an interior surface area 30, and locators 38 removably embedded on an exterior surface area 26. The acupressure glove 42 is adapted to be removably retained on the hand and wrist in a predetermined position relative to acupressure points 75 on the hand 12, 7 and wrist 8 that influence specific physical complaints. As illustrated, the glove 42 includes a plurality of locators 38 positioned to identify the precise site of selected acupressure points 75. The locators 38 are color-coded for easier identification of the correct acupressure point 75 by an individual. The locators 38 are positioned on the glove 42 to identify placement of underlying nodules 39 to which they are removably connected via interlocking female 109 and male components 110 centralized on nodule 39 means and locator 38 means respectively. The glove 42 includes a plurality of nodules 39 that are positioned to depress specific acupressure points 75 and thereby treat the corresponding physical complaint.

Refer now to FIG. 1 which is an overall drawing of the preferred embodiment of the invention from a dorsal perspective. An acupressure glove 42 for the left hand 12 is comprised of an exterior surface area 26, an interior volume 52, an interior surface area 30, an opening 28, locators 38, and nodules 39. Interior volume 52 of acupressure glove 42 is defined as the volume which removably receives a left hand 12 in selected, direct surrounding contact with interior surface area 30 and nodules 39 positioned directly on acupressure points 75. Exterior surface area 26 of glove 42 is defined as the area having locators 38 embedded on its surface. Opening 28 is defined as the access site through which interior surface area 30 and interior volume 52 is accessed by left hand 12.

Figure 2:
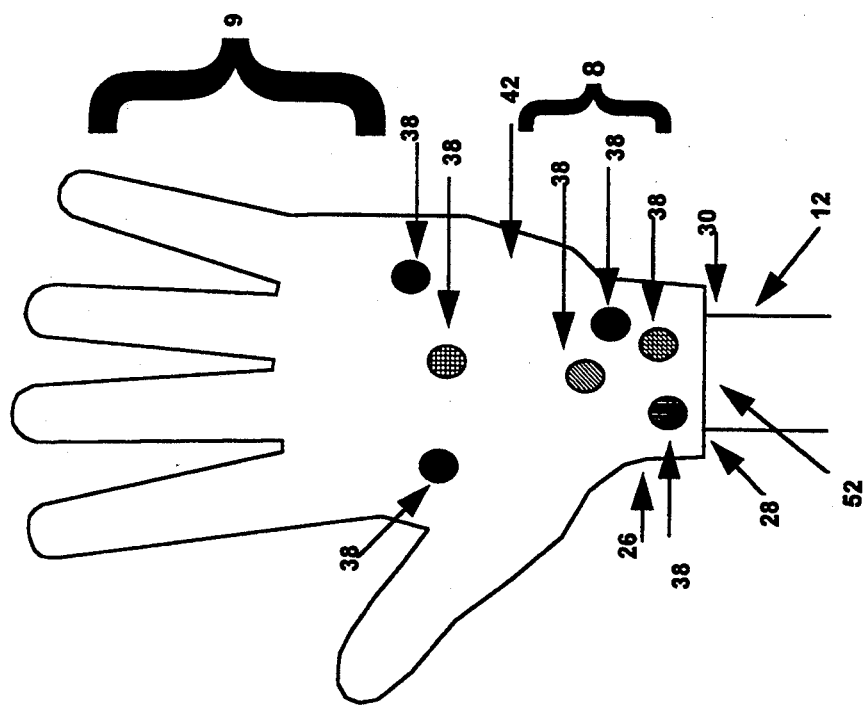
FIG. 2 is a perspective palmar view of the preferred embodiment covering the left hand, wrist, and fingers illustrating the distribution of the acupressure point locators.

FIG. 2 is a palmar view of the acupressure glove 42 for the left hand 12. The acupressure glove 42 consists of an exterior surface area 26, an exterior volume 52, an interior surface area 30, an opening 28, locators 38, and nodules 39. Interior volume 52 of acupressure glove 42 is defined as the volume which removably receives a left hand 12 in selected, direct surrounding contact with interior surface area 30. Exterior surface area 26 of acupressure glove 42 is defined as the area having locators 38 embedded on its surface. Opening 28 is defined as the access site through which interior surface area 30 and interior volume 52 is accessed by left hand 12.

Figure 3:
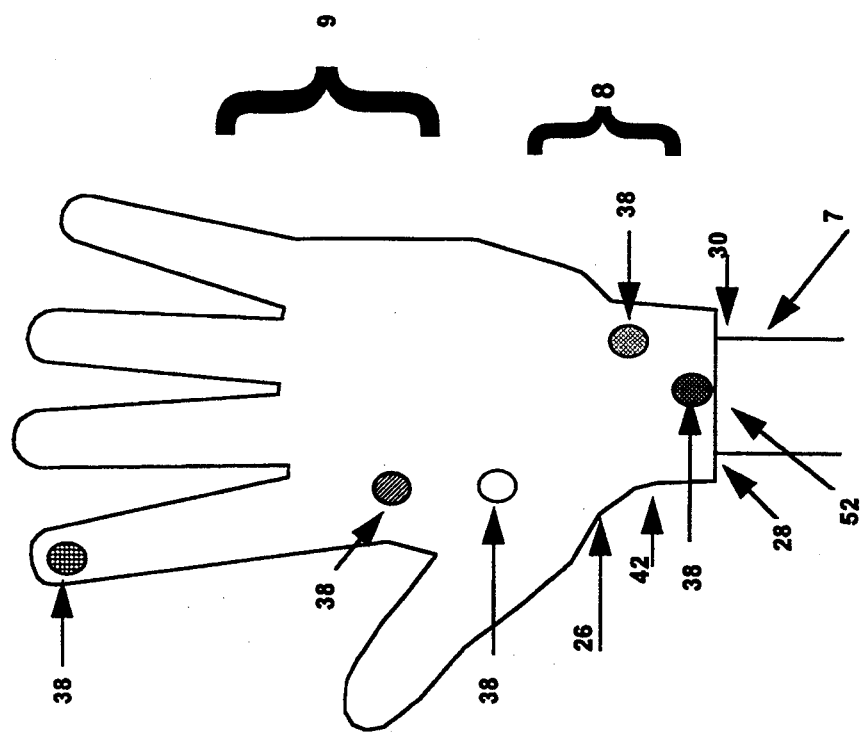
FIG. 3 is a perspective dorsal view of the preferred embodiment covering the right hand and illustrating the distribution of the acupressure point locators.

FIG. 3 is a dorsal perspective of the acupressure glove 42 for the right hand 7. This is a mirror-image of FIG. 1 illustrating the distribution of locators 38 for the right hand. 7. All other aspects of the glove 42 for the right hand 7 are the same as the glove 42 for the left hand 12 as previously described.

Figure 4:
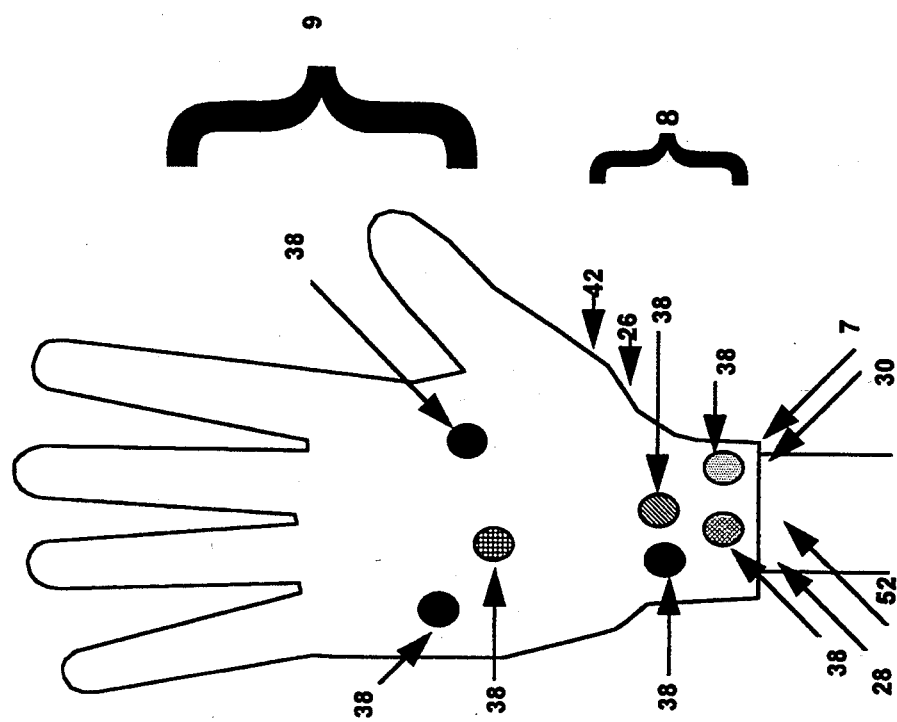
FIG. 4 is a perspective palmar view of the preferred embodiment covering the right hand and illustrating the distribution of the acupressure point locators.

FIG. 4 is a palmar perspective of the acupressure glove 42, for the right hand 7. This is a mirror-image of FIG. 2 illustrating the distribution of locators 38 for the right hand. 7. All other aspects of the glove 42 for the right hand 7 are the same as the glove 42 for the left hand 12 as previously described.

Figure 5:
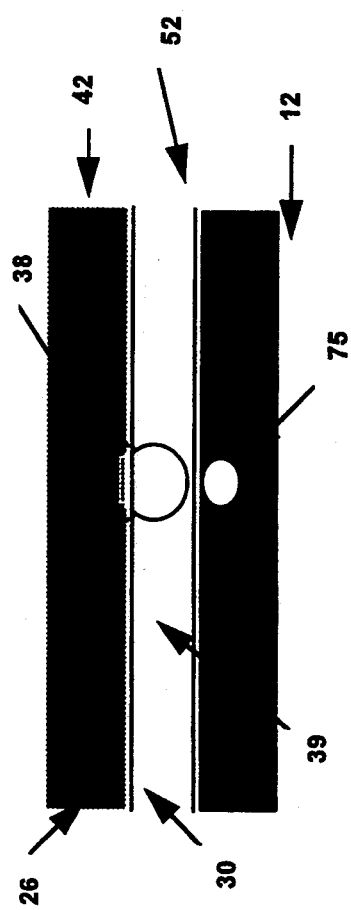
FIG. 5 is a cross-section of the preferred embodiment's exterior surface area with locators and interior surface area with nodules contacting an acupressure point.

FIG. 5 is a cross-section of the exterior surface area 26 with locators 38, interior surface area 30 with nodules 39, and acupressure point 75. This illustrates the connection between the locator 38 and nodule 39 as well as the positioning of the locator 38 and nodule 39 over the acupressure point 75.

Figure 6:
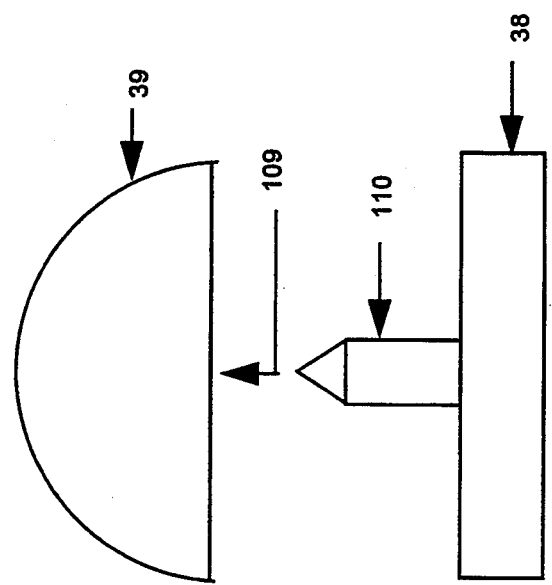
FIG. 6 is an exploded view of a cross-section of the preferred embodiment of a nodule and attaching locator with its male component.

FIG. 6 is an exploded view of the preferred embodiment of a nodule 39 and corresponding locator 38. The locator 38 has a centralized male component 110 positioned on one side forming a round, solid shaft that narrows to a point at its most distal end, this shaft can be inserted and removed from the female component 109 within the nodule 39. The nodule is not less than 10 millimeters in diameter and is spherical in shape with one side being flat.

Figure 7:
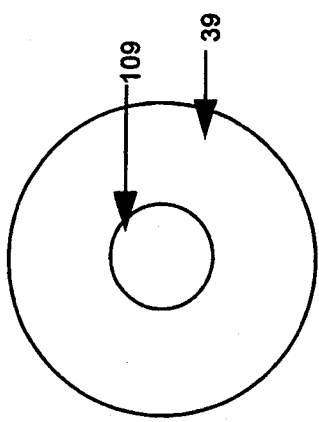
FIG. 7 is an exploded view of a cross-section of the nodule depicted in FIG. 6 illustrating its female component.

FIG. 7 is an exploded view illustrating the female component 109 of the nodule 39 positioned centrally on the flat side forming a hollow, tube-like area within the nodule 39 approximately with an open end and a closed end, the open end allowing for insertion and removal of the male component 110 on the locator 38.

Figure 8:
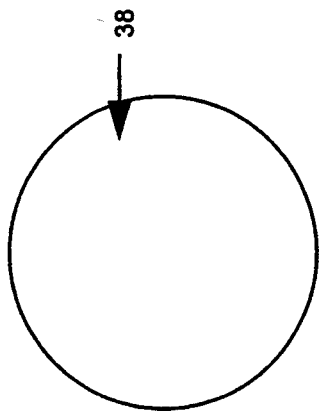
FIG. 8 is an exploded view of a top perspective view of the locator depicted in FIG. 6.

FIG. 8 in an exploded view outlining the shape of the locator 38 showing it to be round in shape and not less than 10 millimeters in diameter.

Figure 9:
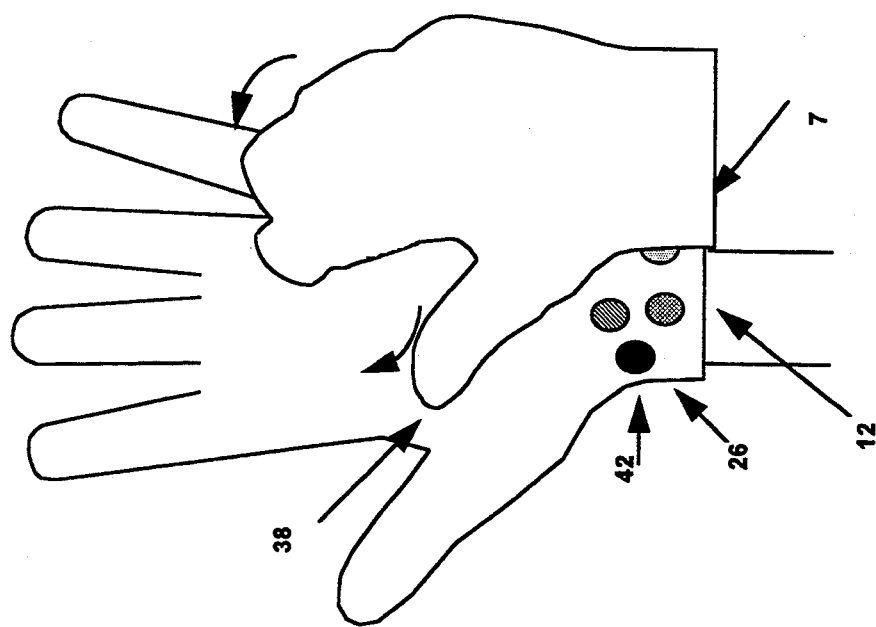
FIG. 9 is a dynamic three dimensional representation illustrating how the right hand is overlaying the acupressure glove worn on the individuals left hand and is applying direct pressure to a locator.

FIG. 9 illustrates an individual inputting dynamic acupressure point stimulation through the glove 42 using the opposite hand 7. After first identifying the appropriate acupressure point 75 to treat, the individual mildly presses on the corresponding locator thus applying direct pressure and therefore stimulation to the underlying acupressure point 75 via the nodule 39 on the interior surface area 30. This figure shows an individual applying direct pressure to a locator on the palmar exterior surface area 26 on the glove 42 for the left hand 12. The thumb of the individual's right hand 7 is applying direct pressure while the fingers 9 of the right hand 7 are wrapped around the dorsal side applying a counter pressure. The individual would also apply direct pressure and therefore stimulation to the same acupressure point 75 on the opposite hand 12 or wrist 8 using the same procedure. This figure illustrates an improved method for an individual to self apply dynamic hand 12, 7 and wrist 8 acupressure point 75 stimulation by placing a flexible, elastic material glove 42 on both hands 12,7 and wrist 8, resulting in gloved hands 12, 7 and wrists 8. The glove 42 has an interior surface area 30, an exterior surface area 26, and specifically located nodules 39 on the interior surface area 30 removably connected to color-coded locators 38 on the exterior surface area 26. FIG. 10 depicts particular acupressure points 75 on the hand 12, 7, wrist 8, and fingers 9 as well as the associated physical complaint. The acupressure points 75 are labeled using their accepted abbreviations and are assigned a color code. For carpal tunnel syndrome, an individual would stimulate P8, P7, H8, and P6 acupressure points 75. For tennis and golfer's elbow, an individual would stimulate L11, L14, and TW 5 acupressure points 75. For general pain, an individual would stimulate L11, and L14 acupressure points 75. For acute neck pain an individual would stimulate the knuckle point, L14 and TW5 acupressure points 75 and for chronic neck pain would also stimulate S13 and L7 acupressure points. For headache, an individual would stimulate P6, H7 and L14 acupressure points 75. For stress and anxiety, an individual would stimulate P6, H7 and L14 acupressure points 75. A guide with this information as well as how to use this invention would be provided for use by an individual. Physical complaints treatable by applying acupressure therapy with this invention comprising carpal tunnel syndrome, general pain, headache, golfers and tennis elbow, acute and chronic neck pain, stress and anxiety relative to the acupressure points 75 on the hands and wrists 8 as described in FIG. 10. Whereby, an individual can utilize the most safe accurate, and cost-effective self-application of acupressure therapy possible in accordance with modern day knowledge.

Figure 11:
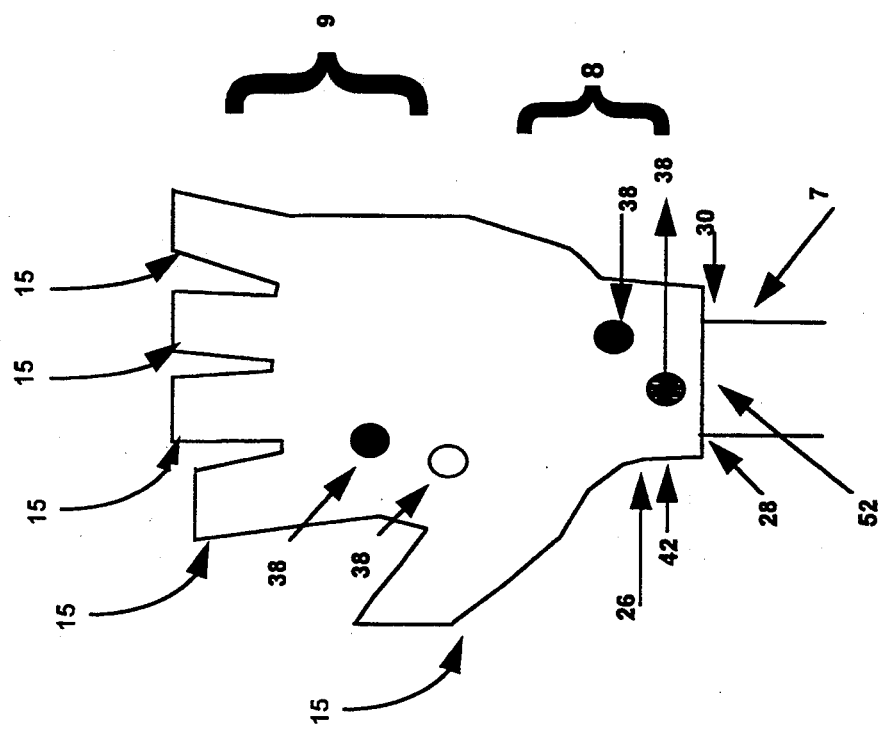
FIG. 11 is a dorsal view of an alternate embodiment showing the fingers of the right handed glove not extending beyond the proximal interphalangeal joint.

FIG. 11 is a dorsal perspective of an alternate embodiment with the fingers 9 of the glove 42 for the right hand 7 not extending beyond the proximal interphalangeal joint 15. This alternate embodiment does omit the acupressure point 75, L11, at the distal end of the second finger 9. Otherwise, this alternate embodiment is unchanged when compared to the preferred embodiment.

Figure 12:
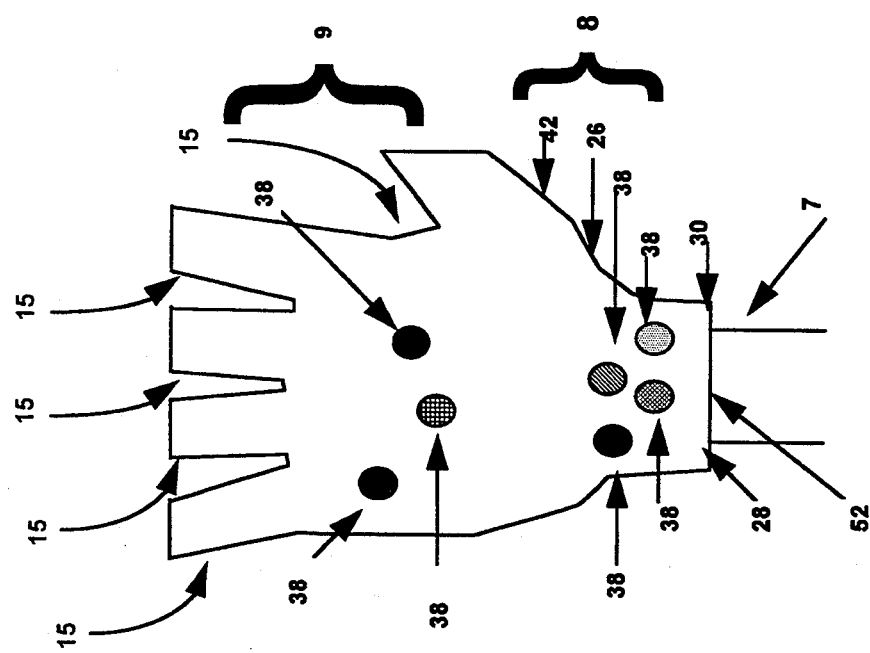
FIG. 12 is a palmar view of an alternate embodiment showing the fingers of the right handed glove not extending beyond the proximal interphalangeal joint.

FIG. 12 is a palmar perspective of the alternate embodiment as described in the above paragraph. The glove 42 from this perspective is unchanged from the preferred embodiment with the exception of the fingers 9 of the glove 42 not extending beyond the proximal interphalangeal joint 15. Both FIG. 11 and FIG. 12 alternate embodiments allow an individual to comfortably work, for instance, at a keyboard, with the tips of the fingers 9 uncovered. This alternate embodiment of the present invention would also allow more body heat to be dissipated making the glove 42 more comfortable to wear.

In use, the individual selects the appropriate-sized gloves 42. The individual then pulls both gloves 42 on snugly. After referring to the guide as previously illustrated in FIG. 10, the individual determines which acupressure point(s) 75 to treat for a particular physical complaint. The color-coded locators 38 aid the individual in correctly selecting the appropriate acupressure points 75. The individual can either remove the other unnecessary locators 38 and nodules 39 or keep the glove 42 whole. Locators 38 and nodules 39 are easily removed and replaced. Once the individual has determined the correct acupressure points 75 to treat, he or she applies mild, direct pressure for a total of approximately 30 seconds to each corresponding locator 38 on both hands 12,7. Treatment of each acupressure point 75 can be repeated up to three times daily.

The foregoing description of the preferred and alternate embodiments of the invention have been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An Acupressure treatment device comprising: an elastic, flexible form capable of conforming to a human hand and wrist, said form adopted to be removably retained on said hand and wrist in a pre-determined position relative to acupressure points on said hand and wrist and influencing specific physical complaints to be treated; and nodule means removably embedded on an interior surface area of said form, and locator means removably embedded on an exterior surface area on said form said nodule means not less than about 10 millimeters in diameter, said nodule means positioned on said form to depress at least one of said specific acupressure points and thereby treat said corresponding physical complaint, when said form is retained in said predetermined position on said hand and wrist said locator means not less than about 10 millimeters in diameter said locator means positioned on said form and removably connected via interlocking female and male components centralized on nodule means and locator means respectively to said nodule means said locator means positioned on said form to identify placement of underlying said nodule means said locator means positioned on said form to identify precise site of said acupressure point on said hand and wrist, when said form is retained in said predetermined position on said hand and wrist said locator means are color-coded for easier identification of correct said acupressure point by said individual, each color correlating to a particular said acupressure point said acupressure points of the said hand and wrist comprising P6, P7, H7, H8, P8, TW5, L14, L11, S16, knuckle point, L7, S13 said form being comprised of an elastic, flexible material.

2. The apparatus as recited in claim 1 wherein said nodule means are spherical in shape with one side being flat, comprising said female component positioned centrally on the flat side forming a hollow, tube-like area within said nodule means with an open end and a closed end, the open end allowing for insertion and removal of said male component on the said locator means.

3. The apparatus as recited in claim 1 wherein said form includes a plurality of said nodule means positioned to depress by direct pressure and thereby stimulate selected of said acupressure points.

4. The apparatus as recited in claim 1 wherein said locator means are round in shape, comprising a centralized said male component positioned on one side forming a solid, round shaft that narrows at its distal end to a point, with the shaft able to be inserted into and removed from said female component within said nodule means.

5. The apparatus as recited in claim 1 wherein said form includes a plurality of said locator means positioned to identify selected of said acupressure points, and to which direct pressure is applied to stimulate said acupressure points via said nodule means.

6. A method of self-applying acupressure therapy to one's hands and wrists using a glove, specifically located nodule means, specifically located color-coded locators means, and a guide containing information regarding which acupressure point or points to stimulate for treatment of the associated physical complaint as well as the color-code of each acupressure point, said method comprising the steps of:

(a) placing a flexible, elastic material said glove on both said hands and wrist, said glove having an interior surface area, an exterior surface area and specifically positioned said nodule means on the interior surface area removably connected to color-coded said locator means to the exterior surface area of said glove;

(b) referring to said guide to determine which said acupressure point or points to stimulate to treat a particular physical complaint;

(c) removing or ignoring the other unnecessary said locator means and said nodule means that do not apply for the particular physical complaint;

(d) applying direct pressure on the corresponding said locator means, and to the said nodule means thus stimulating the underlying said acupressure point;

(e) applying direct pressure for a total of approximately 30 seconds to each corresponding said locator means on both said hands and wrists, thereby self-applying said acupressure therapy.

* * * * *